(12) United States Patent
Garcia-Gabin et al.

(10) Patent No.: US 10,207,801 B2
(45) Date of Patent: Feb. 19, 2019

(54) INSPECTING A SOLAR PANEL USING AN UNMANNED AERIAL VEHICLE

(71) Applicant: ABB Schweiz AG, Baden (CH)

(72) Inventors: Winston Garcia-Gabin, Solna (SE); Bengt Stridh, Västerås (SE); Elina Vartiainen, Västerås (SE); Kari Saarinen, Västerås (SE); Per-Erik Modén, Västerås (SE); Veronika Domova, Västerås (SE)

(73) Assignee: ABB Schweiz AG, Baden (CH)

( * ) Notice: Subject to any disclaimer, the term of this patent is extended or adjusted under 35 U.S.C. 154(b) by 0 days.

(21) Appl. No.: 15/537,162

(22) PCT Filed: Dec. 17, 2014

(86) PCT No.: PCT/EP2014/078236
§ 371 (c)(1),
(2) Date: Jun. 16, 2017

(87) PCT Pub. No.: WO2016/095985
PCT Pub. Date: Jun. 23, 2016

(65) Prior Publication Data
US 2017/0349279 A1    Dec. 7, 2017

(51) Int. Cl.
*B64C 39/02* (2006.01)
*G05D 1/00* (2006.01)
(Continued)

(52) U.S. Cl.
CPC ............ *B64C 39/024* (2013.01); *F24S 40/00* (2018.05); *G01N 21/88* (2013.01); *G05D 1/0094* (2013.01);
(Continued)

(58) Field of Classification Search
CPC ........ B64C 39/024; H02S 50/10; G01N 21/88; G06K 9/00637
See application file for complete search history.

(56) References Cited

U.S. PATENT DOCUMENTS

2010/0043870 A1   2/2010   Bennett et al.
2010/0215212 A1   8/2010   Flakes, Jr.
(Continued)

FOREIGN PATENT DOCUMENTS

WO      2014029431 A1    2/2014

OTHER PUBLICATIONS

Quater et al., Light Unmanned Aerial Vehicles (UAVs) for Cooperative Inspection of PV Plants. (IEEE Journal of Photovoltaics, vol. 4, No. 4, Jul. 2014. pp. 1107-1113.*
(Continued)

*Primary Examiner* — Obafemi O Sosanya
(74) *Attorney, Agent, or Firm* — Whitmyer IP Group LLC

(57) ABSTRACT

A method for inspecting a solar panel of a solar power station is performed in a controller for an unmanned aerial vehicle, UAV, and includes the steps of: receiving an inspection request for a subset of the solar panels navigating, in a first stage, using radio signals, the UAV to an initial location in a vicinity of a particular solar panel of the subset of solar panels; positioning, in a second stage, the UAV using at least one near field sensor of the UAV; and capturing, using the infrared camera, an image of the particular solar panel.

20 Claims, 4 Drawing Sheets

(51) Int. Cl.
*H02S 50/10* (2014.01)
*G01N 21/88* (2006.01)
*G06K 9/00* (2006.01)
*F24S 40/00* (2018.01)

(52) U.S. Cl.
CPC .......... *G06K 9/00637* (2013.01); *H02S 50/10* (2014.12); *Y02E 10/40* (2013.01)

(56) References Cited

U.S. PATENT DOCUMENTS

| | | | |
|---|---|---|---|
| 2012/0175468 A1* | 7/2012 | Zerof | A62C 3/0228 |
| | | | 244/190 |
| 2012/0242321 A1* | 9/2012 | Kasai | G01J 5/0066 |
| | | | 324/72 |
| 2014/0034776 A1 | 2/2014 | Hutson | |
| 2016/0004795 A1* | 1/2016 | Novak | G06F 17/5009 |
| | | | 703/1 |

OTHER PUBLICATIONS

Tom Lombardo: "UAVs to Inspect Solar Farms", Engineering.com Published: May 4, 2014; Retrieved from the Internet: http://www.engineering.com/ElectronicsDesign/ElectronicsDesignArticles/ArticleID/7544/UAVs-to-Inspect-Solar-Farms.aspx; Retrieved on Jun. 9, 2017.

International Preliminary Report on Patentability Application No. PCT/EP2014/078236 dated Nov. 21, 2016 5 Pages.

International Search Report & Written Opinion Application No. PCT/EP2014/078236 Completed: Oct. 8, 2015; dated Oct. 14, 2015 11 Pages.

* cited by examiner

INSPECTING A SOLAR PANEL USING AN UNMANNED AERIAL VEHICLE

TECHNICAL FIELD

The invention relates to inspecting a solar panel of a solar power station. In particular, this invention relates to a method, unmanned aerial vehicle (UAV) controller, UAV, computer program and computer program product for using an UAV to inspect a particular solar panel.

BACKGROUND

There is an ever increasing demand in environment friendly energy sources. One area of great development is solar power. Solar power in a solar power station can be harvested without the need for any fuel to operate and provides a very low carbon dioxide footprint. Moreover, when the solar power station is installed in a location where cloud coverage is low, the solar power output can be reliable and predictable.

However, solar panels, e.g. of photovoltaic solar power stations, are subject to failures, due to e.g. weather or component failures.

In an article named "UAVs to Inspect Solar Farms", Tom Lombardo, 4 May 2014, Engineering.com Electronics, available at http://www.engineering.com/ElectronicsDesign/ElectronicsDesignArticles/ArticleID/7544/UAVs-to-Inspect-Solar-Farms.aspx at the time of filing this application, it is disclosed that a UAV has been developed that is used for remote monitoring and inspection of construction sites, mining operations, and farms. This UAV is now being used in the solar array inspection business and will be tested on photovoltaic farms using an infrared thermal imaging camera. However, capturing such data of sufficient quality requires skill and experience of an operator flying the UAV.

US 2010/0215212 A1 discloses a system and method utilizing an unmanned air vehicle to inspect structures. An unmanned air vehicle capable of moving to a position and hovering in place is positioned using GPS coordinates. The unmanned air vehicle is able to capture images of the structure and transmit the images to an inspector and a database. Data identifying the position of the unmanned air vehicle and the orientation of the digital camera can be stored in the database, permitting specific inspections of specific structural elements to be repeated with a high degree of precision and accuracy later in time.

SUMMARY

It is an object to provide a way to allow automatic capturing of images for inspection of a solar panel.

According to a first aspect, it is presented a method for inspecting a solar panel of a solar power station. The method is performed in a controller for an unmanned aerial vehicle, UAV, and comprises the steps of: receiving an inspection request for a subset of the solar panels; navigating, in a first stage, using radio signals, the UAV to an initial location in a vicinity of a particular solar panel of the subset of solar panels; positioning, in a second stage, the UAV using at least one near field sensor of the UAV; and capturing, using the infrared camera, an image of the particular solar panel. Using the two stage navigation of the UAV to inspect a particular solar panel, the UAV does not need to be manually controlled which is a significant advantage over the prior art. Using automatic control, the UAV could be automatically controlled to a site of a detected fault, reducing any latency involved when a human operator needs to recognise the fault, initialise the UAV and fly the UAV to the site of the error. Additionally, regular inspection rounds can be scheduled without the need for constant operator monitoring.

The step of positioning may comprise positioning the UAV such that an infrared camera of the UAV is as close as possible, within a margin of error, to a direction being perpendicular to a main surface of the particular solar panel while preventing the UAV from shadowing the particular solar panel.

In the step of receiving, the subset of solar panels may comprise a plurality of solar panels; in which case the steps of navigating, positioning and capturing are repeated for each solar panel of the subset of solar panels.

In the step of navigating, the radio signals may be satellite based radio signals.

In the step of navigating, the radio signals may be ground based radio signals from radio beacons.

In the step of positioning, the at least one near field sensor may comprise at least one of: a camera, a radar device, and an ultrasound scanner.

The method may further comprise the step of: determining the initial location based on the inspection request, wherein the inspection request comprises an identifier of the subset of solar panels.

The method may further comprise the step of: transmitting the image to a control centre.

The method may further comprise the step of: identifying a fault by analysing the image of the particular solar panel.

According to a second aspect, it is presented a controller for an unmanned aerial vehicle, UAV, the controller being arranged to inspect a solar panel of a solar power station. The controller comprises: a processor; and a memory storing instructions that, when executed by the processor, causes the controller to: receive an inspection request for a subset of the solar panels; navigate, in a first stage, using radio signals, the UAV to an initial location in a vicinity of a particular solar panel of the subset of solar panels; position, in second stage, the UAV using at least one near field sensor of the UAV; and capture, using the infrared camera, an image of the particular solar panel.

The instructions to position may comprise instructions that, when executed by the processor, causes the controller to position the UAV such that an infrared camera of the UAV is as close as possible, within a margin of error, to a direction being perpendicular to a main surface of the particular solar panel while preventing the UAV from shadowing the particular solar panel.

The subset of solar panels may comprise a plurality of solar panels; in which case the instructions further comprise instructions that, when executed by the processor, causes the controller to repeat the instructions to navigate, position and capture for each solar panel of the subset of solar panels.

The radio signals may be satellite based radio signals.

The radio signals may be ground based radio signals from radio beacons.

The at least one near field sensor may comprise at least one of: a camera, a radar device, and an ultrasound scanner.

The controller may further comprise instructions that, when executed by the processor, causes the controller to: determine the initial location based on the indication, wherein the indication comprises an identifier of the subset of solar panels.

The controller may further comprise instructions that, when executed by the processor, causes the controller to transmit the image to a control centre.

The controller may further comprise instructions that, when executed by the processor, causes the controller to identify a fault by analysing the image of the particular solar panel.

According to a third aspect, it is presented an unmanned aerial vehicle comprising the controller according to any one of claims 10 to 18.

According to a fourth aspect, it is presented a computer program for inspecting a solar panel of a solar power station. The computer program comprises computer program code which, when run on a controller for an unmanned aerial vehicle, UAV, causes the controller to: receive an inspection request for a subset of the solar panels; navigate, in a first stage, using radio signals, the UAV to an initial location in a vicinity of a particular solar panel of the subset of solar panels; position, in a second stage the UAV using at least one near field sensor of the UAV; and capture, using the infrared camera, an image of the particular solar panel.

According to a fifth aspect, it is presented a computer program product comprising a computer program according to the fourth aspect and a computer readable means on which the computer program is stored.

Generally, all terms used in the claims are to be interpreted according to their ordinary meaning in the technical field, unless explicitly defined otherwise herein. All references to "a/an/the element, apparatus, component, means, step, etc." are to be interpreted openly as referring to at least one instance of the element, apparatus, component, means, step, etc., unless explicitly stated otherwise. The steps of any method disclosed herein do not have to be performed in the exact order disclosed, unless explicitly stated.

BRIEF DESCRIPTION OF THE DRAWINGS

The invention is now described, by way of example, with reference to the accompanying drawings, in which:

FIG. 3 is a schematic diagram of the subset of solar panels of FIG. 2 and an initial location which the UAV can be navigated to;

DETAILED DESCRIPTION

The invention will now be described more fully hereinafter with reference to the accompanying drawings, in which certain embodiments of the invention are shown. This invention may, however, be embodied in many different forms and should not be construed as limited to the embodiments set forth herein; rather, these embodiments are provided by way of example so that this disclosure will be thorough and complete, and will fully convey the scope of the invention to those skilled in the art. Like numbers refer to like elements throughout the description.

Figure 1:
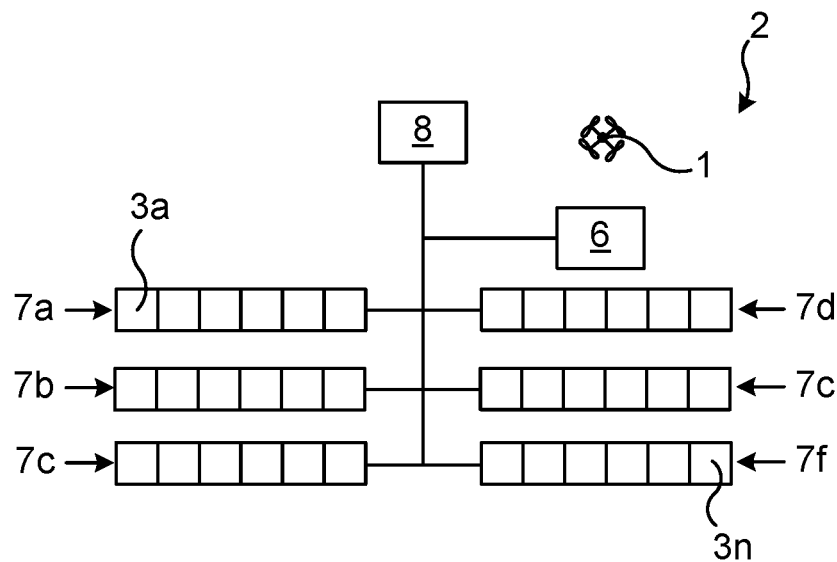
FIG. 1 is a schematic drawing illustrating an environment in which embodiments presented herein can be applied.

FIG. 1 is a schematic drawing illustrating an environment in which embodiments presented herein can be applied. A solar power station 2 comprises n solar panels 3*a*-*n*. The solar panels 3*a*-*n* can e.g. be photovoltaic (PV) solar panels, converting solar power to electric power. The solar panels 3*a*-*n* are arranged in sections 7*a*-*f*. The number of solar panels 3*a*-*n* and the number of sections 7*a*-*f* can vary. For instance, the solar power station could even be arranged with only a single section comprising all the solar panels. The power from the solar panels is aggregated in a connection station 6 which can, e.g. be connected to a DC (Direct Current) link or an AC (Alternating Current) grid. The connection station can e.g. comprise one or more DC/AC converters, one or more transformers, etc. circuit breakers, etc.

One or more of the solar panels 3*a*-*n* may sometimes partly or completely fail. In order to inspect the solar panels 3*a*-*n* an unmanned aerial vehicle (UAV) 1 is utilised. The UAV 1 is also known by other terms, e.g. drone. According to embodiments presented herein, the UAV 1 performs a two stage navigation to inspect a particular solar panel, whereby the UAV 1 does not need to be manually controlled.

A control centre 8 allows monitoring of the operation of the solar power station 2 by an operator. The control centre 8 can be used to detect problems in the power station 2. For instance, the control centre can send commands to the UAV 1 and receive feedback from the UAV 1.

Figure 2:
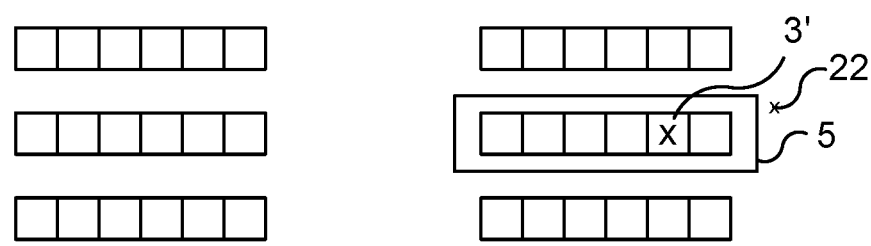
FIG. 2 is a schematic diagram of the solar power station of FIG. 1, illustrating a subset of the solar panels comprising a faulty solar panel.

FIG. 2 is a schematic diagram of the solar power station of FIG. 1, illustrating a subset of the solar panels comprising a faulty solar panel. Here, there is a particular solar panel 3' which has been indicated to be faulty (or potentially faulty) and needs to be inspected. The particular solar panel 3' is part of a subset 5 of solar panels. There is an initial location 22 associated with the subset 5 of solar panels. When inspection is to occur, the UAV 1 first navigates to the initial location 22 associated with the subset 5 of solar panels, after which the UAV 1 can position itself in a good position in order to inspect the particular solar panel 3', e.g. using an infrared (IR) camera.

Figure 3:
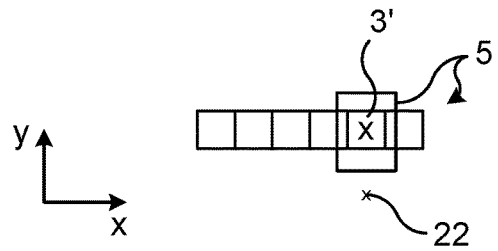

FIG. 3 is a schematic diagram of the subset of solar panels of FIG. 2 and an initial location which the UAV can be navigated to. In this example, the subset of solar panels 5 comprises only the particular solar panel 3' which is the one to be inspected. An x-axis and a y-axis of a coordinate system are indicated also.

Figure 4:
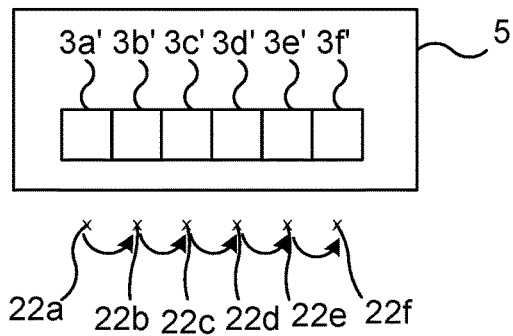
FIG. 4 is a schematic diagram of the subset of solar panels of FIG. 2 and initial locations which the UAV can be navigated to when the identity of the faulty solar panel is not known.

FIG. 4 is a schematic diagram of the subset of solar panels 3*a*'-3*f*' of FIG. 2 and initial locations 22*a*-*f* which the UAV can be navigated to when the identity of the faulty solar panel is not known. Here, a subset 5 of solar panels comprise six solar panels 3*a*'-3*f*'. In this example, all of these six solar panels 3*a*'-3*f*' need to be inspected. For instance, a fault indication might have been received indicating that there is a fault in one section (of the sections 7*a*-*f* of FIG. 1), but without an indication as to which individual solar panel being the cause of the fault. Each of these solar panels 3*a*'-3*f*' corresponds to a respective initial location 22*a*-*f*. When inspecting, the UAV then navigates to the first initial location 22*a*, positions itself using near field sensors, and captures an IR image of the first solar panel 3*a*'. Then the UAV continues to the next initial location 22*b* to perform the same actions, etc. for all initial locations 22c-f. In this way, all of the solar panels 3a'-3f' of the subset are inspected using the UAV to thereby identify the faulty solar panel or solar panels.

Figure 5A:
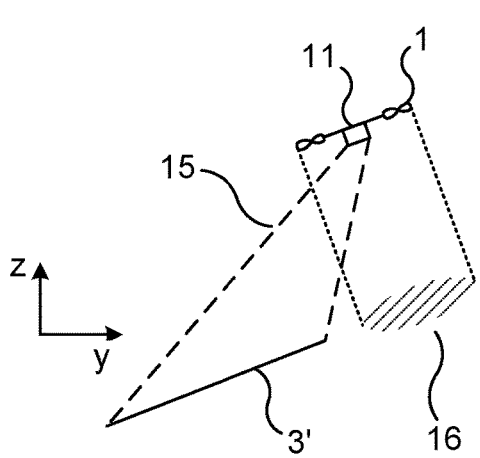
FIGS. 5A-5B are schematic diagrams illustrating positioning of the UAV such that it is perpendicular to a solar panel.
Figure 5B:
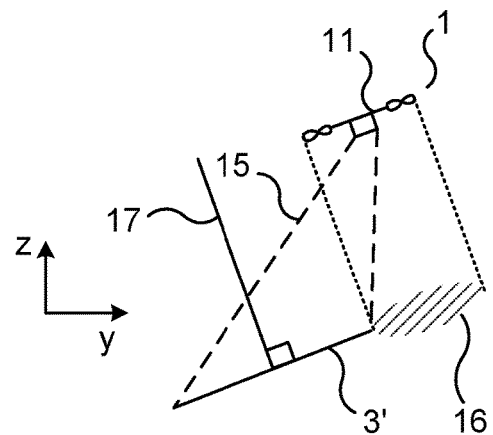

FIGS. 5A-B are schematic diagrams illustrating positioning of the UAV such that it is perpendicular to a solar panel.

A y-axis and z-axis of are indicated, being of the same coordinate system as that of FIG. 3. The solar panel 3' can be angled to maximise surface area towards the sun. The angle may also include an x component, even if this is not shown here. Optionally, the angle of the solar panel 3' can change over time to follow the movement of the sun across the sky.

In FIG. 5A, the UAV 1 comprising an IR camera 11, is positioned by the particular solar panel 3'. However, the UAV 1 is positioned such that an angle of view 15 of the IR camera is not optimal for inspection of the solar panel. An IR image captured at this position would not be optimal to allow errors in the solar panel to be found. Nevertheless, a shadow 16 of the UAV falls outside the particular solar panel 3'

In FIG. 5B, the UAV 1 has positioned itself such that the IR camera 11 is as close as possible, within a margin of error, to a direction 17 being perpendicular to a main surface of the particular solar panel 3'. However, the position is also such that the UAV 1 is prevented from shadowing the particular solar panel 3'. In other words, the shadow 16 of the UAV falls outside the particular solar panel 3', such that the shadow does not distort the IR image which is captured to detect faults. The main surface of the solar panel is the surface intended to face the sun. By positioning itself in this way, the UAV 1 improves the quality of the IR image and thus increases the chances of allowing an error in the solar panel to be identified in the IR image.

The positioning is performed using near field sensors as described in more detail below.

Figure 6:
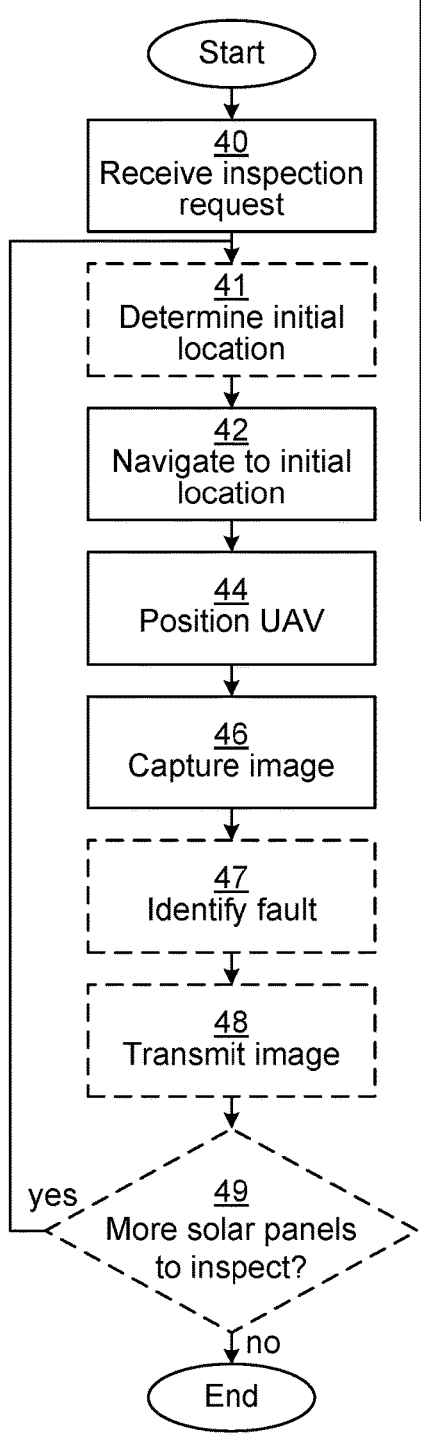
FIG. 6 is a flow chart illustrating embodiments of methods performed in the controller for the UAV for inspecting a solar panel.

FIG. 6 is a flow chart illustrating embodiments of methods performed in the controller for the UAV for inspecting a solar panel of a solar power station, e.g. of FIG. 1. The method is performed in a controller for a UAV.

In a receive inspection request step 40, an inspection request for a subset of the solar panels is received. This can e.g. be received from the control centre when an indication of a fault has been received. Alternatively, all solar panels are inspected from time to time.

In an optional determine initial location step 41, the initial location is determined based on the indication. The indication then comprises an identifier of the subset of solar panels. For instance, each subset of solar panels (or each solar panel) can be associated with a set of coordinates defining an associated initial location. This association can be stored in a data memory (see e.g. data memory 66 of FIG. 7).

In a navigate to initial location step 42, the UAV is navigated, in a first stage, using radio signals, to an initial location in a vicinity of a particular solar panel of the subset of solar panels. The radio signals can be satellite based radio signals from satellites or ground based radio signals from radio beacons as explained in more detail below. This navigation is a first, rough, positioning of the UAV to allow imaging of the particular solar panel.

In a position UAV step 44, the UAV is positioned, in a second stage, using at least one near field sensor of the UAV. This positioning can include positioning the UAV such that an infrared camera of the UAV is as close as possible, within a margin of error, to a direction being perpendicular to a main surface of the particular solar panel, while preventing the UAV from shadowing the particular solar panel. Alternatively or additionally, the positioning is done such that other objects or buildings do not distort an IR image. Such distortion are due to the specular nature of photovoltaic solar panels, where surrounding objects can be seen (mirrored) in the solar panel. The positioning in this step is a finer positioning of the UAV compared to the preceding step. The margin of error could be any suitable deviation from the ideal position. For instance, the margin of error could be 5 degrees to give a relatively accurate imaging of the solar panel. Alternatively, the margin of error could be 15 degrees to allow easier positioning of the UAV. In one embodiment, the margin of error depends on a desired image quality, which in some cases depends on how close to the perpendicular that the IR camera is located. The at least one near field sensor comprises at least one of: a camera, a radar device, and an ultrasound scanner. When the camera is used as a near field sensor, the positioning can be performed in a feedback loop to control the solar panel in a captured image to be a rectangle, i.e. with 90 degree angles of the corners of the image of the solar panel.

In one embodiment, the first stage (step 42) includes only rough navigation using the radio signals, and the second stage (step 44) includes fine positioning using only the near field sensors.

In one embodiment, this step comprises positioning, using the at least one near field sensor, such that an infrared camera of the UAV is located in a direction being perpendicular, within a margin of error, from a centre point of the main surface of the particular solar panel.

Optionally, multiple near field sensors are used in combination to improve accuracy in the positioning, since such sensor fusion can correct for deficiencies of individual sensors to calculate an accurate position.

In a capture image step 46, an image of the particular solar panel is captured using the infrared camera. IR imaging allows many faults in solar panels to be identified since faults often cause temperature variations in the solar panel.

In an optional identify fault step 47, a fault is identified by analysing the image of the particular solar panel. This analysis can comprise image analysis to detect abnormal temperature variations in the particular solar panel. For instance, temperature differences can be characterized and compared to the thresholds. In case of fault, the process continues with fault classification. Faulted areas are isolated and characterised by factors such as temperature profile, size, shape and number of faulted cells. On the basis of the characteristics, it can be determined which fault type group the detected fault belongs to. This determination can divide the characteristics space into mutually exclusive regions defined during a training phase. The number of the regions equals the number of the fault types. The assigning rule such as Bayes rule, decides in which fault group the isolated faulted area with particular set of measured characteristics belongs.

In an optional transmit step 48, the image is transmitted to a control centre. When the identify fault step 47 is performed, this step can comprise also transmitting an indication of the identified fault. The transmission to the control centre can occur wirelessly during flight or when the UAV has landed, or using wire based communication when the UAV has landed, e.g. in a docking station.

As explained above with reference to FIG. 4, the subset of solar panels can be a single solar panel or comprise a plurality of solar panels. In an optional conditional more solar panels to inspect step 49, it is determined whether there are any more solar panels to inspect in the subset of solar panels. If this is true, the method returns to the determine initial location step 41, or if this step is not executed, to the navigate to initial location step 42. When returning, the reiterated steps are performed for a new solar panel being the particular solar panel. If there are no more solar panels to inspect, the method ends.

By first navigating to the initial location followed by the more accurate positioning perpendicular to the particular solar panel to allow an accurate image capture, the process of capturing images of solar panels can be automated while keeping image quality at a high level for fault detection. This eliminates the need for inaccurate and labour intensive manual control of the UAV for solar panel inspection.

Figure 7:
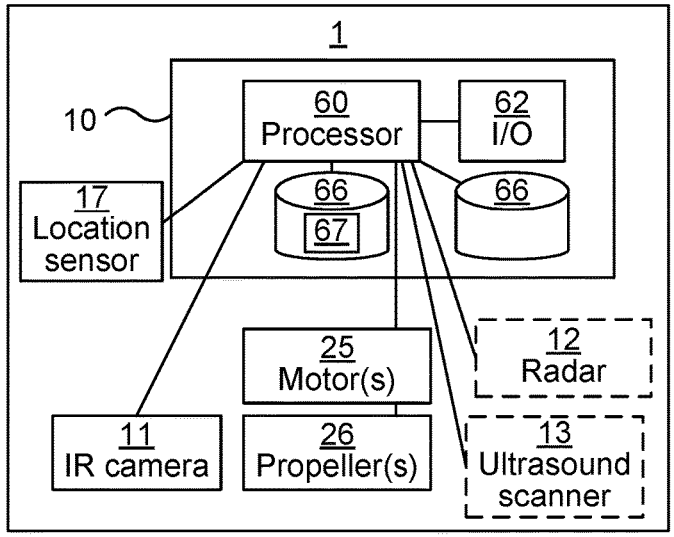
FIG. 7 is a schematic diagram showing some components of the UAV of FIG. 1 according to one embodiment.

FIG. 7 is a schematic diagram showing some components of the UAV of FIG. 1 according to one embodiment. The UAV comprises one or more motors 25, each connected to one or more propellers 26, allowing the UAV to fly.

An IR camera 11 is used to capture infrared images of solar panels to allow fault identification. Optionally, the IR camera 11 is also used as an input to allow positioning of the UAV (and the IR camera 11 itself in particular) essentially perpendicularly to the main surface of the solar panel to inspect. Alternatively or additionally, a radar 12 and an ultrasound sensor 13 can be used to position the UAV (and the IR camera 11) essentially perpendicularly to the main surface of the solar panel to inspect.

A location sensor 17 detects the position of the UAV using radio signals. As explained below, the location sensor can use satellite originated radio signals and/or ground based radio signals from radio beacons.

The UAV 1 is controlled by a controller 10. The controller 10 is here shown as part of the UAV 1, but could in principle be located externally to the UAV 1. A processor 60 of the controller 10 is provided using any combination of one or more of a suitable central processing unit (CPU), multiprocessor, microcontroller, digital signal processor (DSP), application specific integrated circuit etc., capable of executing software instructions 67 stored in a memory 65 of the controller 10, which memory 65 can thus be a computer program product. The processor 60 can be configured to execute the method described with reference to FIG. 6 above.

The memory 65 can be any combination of read and write memory (RAM) and read only memory (ROM). The memory 65 also comprises persistent storage, which, for example, can be any single one or combination of magnetic memory, optical memory, solid state memory or even remotely mounted memory.

A data memory 66 is also provided for reading and/or storing data during execution of software instructions in the processor 60. For instance, the data memory 66 can store coordinates of the initial location and/or image data. The data memory 66 can be any combination of read and write memory (RAM) and read only memory (ROM).

The controller 10 further comprises an I/O interface 62 for communicating with other external entities. Optionally, the I/O interface 62 also includes a user interface. The I/O interface 62 can comprise one or more transceivers, comprising analogue and digital components, and a suitable number of antennas for wireless communication of a communication channel to the control centre 8. Alternatively or additionally, the I/O interface 62 comprises ports for wire based communication with the control centre 8, e.g. using Universal Serial Bus (USB), FireWire, Ethernet, etc.

Other components of the UAV 1 are omitted here in order not to obscure the concepts presented herein.

Figure 8A:
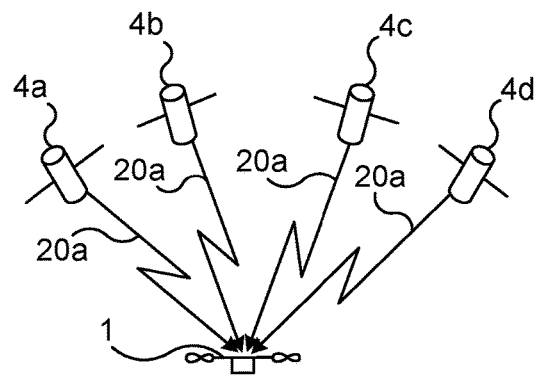
FIGS. 8A-8B are schematic diagrams illustrating embodiments of the use of radio signals for navigation in the UAV of FIG. 1.
Figure 8B:
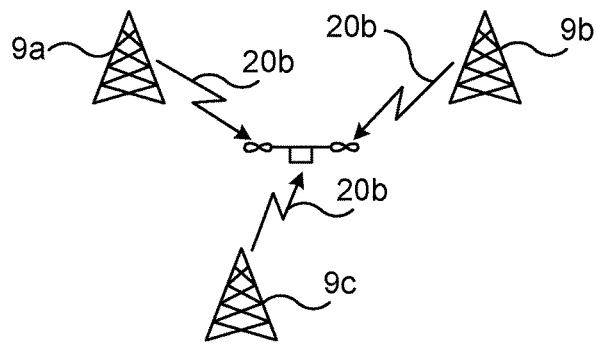

FIGS. 8A-B are schematic diagrams illustrating embodiments of the use of radio signals for navigation in the UAV of FIG. 1. In FIG. 8A, four satellites 4*a-d* are shown transmitting satellite based radio signals 20*a* for a Global Navigation Satellite System (GNSS), such as Global Positioning System (GPS). This allows the UAV 1 to navigate, e.g. to one or more initial locations as described above without the need for any new installations for this navigation. While there are here four satellites shown, more or fewer satellites can be utilised.

In FIG. 8B, three ground based radio beacons 9*a-c* are shown transmitting ground based radio signals 20*b* for ground based positioning. While this embodiment relies on the installation of the ground based radio beacons 9*a-c*, perhaps even at the solar power station, such a system can provide greater accuracy for the positioning of the UAV 1 compared to satellite based positioning. This allows the UAV 1 to navigate, e.g. to one or more initial locations as described above. While there are here three ground based radio beacons shown, more beacons can be utilised. The positioning in this embodiment can e.g. utilise time-difference-of-arrival measurements of ultra wideband (UWB) pulses.

Figure 9:
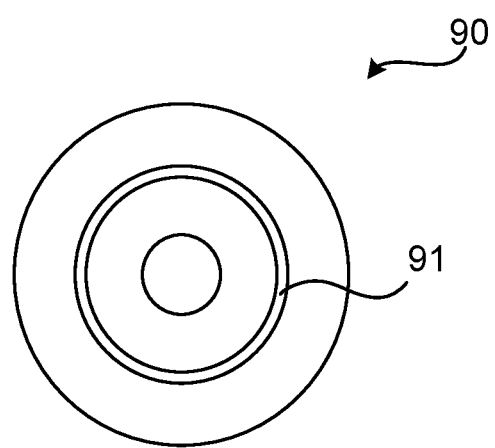
FIG. 9 shows one example of a computer program product comprising computer readable means.

FIG. 9 shows one example of a computer program product comprising computer readable means. On this computer readable means a computer program 91 can be stored, which computer program can cause a processor to execute a method according to embodiments described herein. In this example, the computer program product is an optical disc, such as a CD (compact disc) or a DVD (digital versatile disc) or a Blu-Ray disc. As explained above, the computer program product could also be embodied in a memory of a device, such as the computer program product 65 of FIG. 7. While the computer program 91 is here schematically shown as a track on the depicted optical disk, the computer program can be stored in any way which is suitable for the computer program product, such as a removable solid state memory, e.g. a Universal Serial Bus (USB) drive.

The invention has mainly been described above with reference to a few embodiments. However, as is readily appreciated by a person skilled in the art, other embodiments than the ones disclosed above are equally possible within the scope of the invention, as defined by the appended patent claims.

The invention claimed is:

1. A method for inspecting a solar panel of a solar power station, the method being performed in a controller for an unmanned aerial vehicle, UAV, and comprising the steps of:
   receiving an inspection request for a subset of solar panels of the solar power station;
   navigating, in a first stage, using radio signals, the UAV to an initial location in a vicinity of a particular solar panel of the subset of solar panels;
   positioning, in a second stage, the UAV using at least one near field sensor of the UAV, such that an infrared camera of the UAV is disposed as close as possible, within a margin of error, to a direction being perpendicular to a main surface of the particular solar panel while preventing the UAV from shadowing the particular solar panel; and
   capturing, using the infrared camera, an image of the particular solar panel.

2. The method according to claim 1, wherein in the step of receiving, the subset of solar panels comprises a plurality of solar panels; and wherein the steps of navigating, positioning and capturing are repeated for each solar panel of the subset of solar panels.

3. The method according to claim 1, wherein in the step of navigating, the radio signals are satellite based radio signals.

4. The method according to claim 1, wherein in the step of navigating, the radio signals are ground based radio signals from radio beacons.

5. The method according to claim 1, wherein in the step of positioning, the at least one near field sensor comprises at least one of: a camera, a radar device, and an ultrasound scanner.

6. The method according to claim 1, further comprising the step of:
   determining the initial location based on the inspection request, wherein the inspection request comprises an identifier of the subset of solar panels.

7. The method according to claim 1, further comprising the step of:
   transmitting the image to a control centre.

8. The method according to claim 1, further comprising the step of:
   identifying a fault by analysing the image of the particular solar panel.

9. A controller for an unmanned aerial vehicle, UAV, the controller being arranged to inspect a solar panel of a solar power station, the controller comprising:
   a processor; and
   a memory storing instructions that, when executed by the processor, causes the controller to:
   receive an inspection request for a subset of solar panels of the solar power station;
   navigate, in a first stage, using radio signals, the UAV to an initial location in a vicinity of a particular solar panel of the subset of solar panels;
   position, in a second stage, the UAV using at least one near field sensor of the UAV, such that an infrared camera of the UAV is disposed as close as possible, within a margin of error, to a direction being perpendicular to a main surface of the particular solar panel while preventing the UAV from shadowing the particular solar panel; and
   capture, using the infrared camera, an image of the particular solar panel.

10. The controller according to claim 9, wherein the subset of solar panels comprise a plurality of solar panels; and wherein the instructions further comprise instructions that, when executed by the processor, causes the controller to repeat the instructions to navigate, position and capture for each solar panel of the subset of solar panels.

11. The controller according to claim 9, wherein the radio signals are satellite based radio signals.

12. The controller according to claim 9, wherein the radio signals are ground based radio signals from radio beacons.

13. The controller according to claim 9, wherein the at least one near field sensor comprises at least one of: a camera, a radar device, and an ultrasound scanner.

14. The controller according to claim 9, further comprising instructions that, when executed by the processor, causes the controller to: determine the initial location based on the indication, wherein the indication comprises an identifier of the subset of solar panels.

15. The controller according to claim 9, further comprising instructions that, when executed by the processor, causes the controller to transmit the image to a control centre.

16. The controller according to claim 9, further comprising instructions that, when executed by the processor, causes the controller to identify a fault by analysing the image of the particular solar panel.

17. An unmanned aerial vehicle comprising the controller according to claim 9.

18. A computer program for inspecting a solar panel of a solar power station, the computer program comprising computer program code which, when run on a controller for an unmanned aerial vehicle, UAV, causes the controller to:
   receive an inspection request for a subset of solar panels of the solar power station;
   navigate, in a first stage, using radio signals, the UAV to an initial location in a vicinity of a particular solar panel of the subset of solar panels;
   position, in a second stage the UAV using at least one near field sensor of the UAV, such that an infrared camera of the UAV is disposed as close as possible, within a margin of error, to a direction being perpendicular to a main surface of the particular solar panel while preventing the UAV from shadowing the particular solar panel; and
   capture, using the infrared camera, an image of the particular solar panel.

19. A computer program product comprising a computer program according to claim 18 and a computer readable means on which the computer program is stored.

20. The controller according to claim 10, wherein the radio signals are satellite based radio signals.

* * * * *